(12) United States Patent
Fuchs et al.

(10) Patent No.: US 9,709,570 B2
(45) Date of Patent: Jul. 18, 2017

(54) METHOD AND DEVICE FOR MARKING ISOTOPES

(71) Applicant: BASF PLANT SCIENCE COMPANY GMBH, Ludwigshafen (DE)

(72) Inventors: Regine Fuchs, Berlin (DE); Olaf Woiwode, Michendorf (DE); Enrico Peter, Berlin (DE); Hardy Schön, Berlin (DE); Christoph Wittmann, Wolfenbuettel (DE); Detlev Rasch, Braunschweig (DE); Veronique Beckers, Braunschweig (DE); Lisa Dersch, Braunschweig (DE)

(73) Assignee: BASF PLANT SCIENCE COMPANY GMBH, Ludwighshafen (DE)

( * ) Notice: Subject to any disclaimer, the term of this patent is extended or adjusted under 35 U.S.C. 154(b) by 0 days.

(21) Appl. No.: 14/441,536

(22) PCT Filed: Nov. 7, 2013

(86) PCT No.: PCT/EP2013/073245
§ 371 (c)(1),
(2) Date: May 8, 2015

(87) PCT Pub. No.: WO2014/079696
PCT Pub. Date: May 30, 2014

(65) Prior Publication Data
US 2015/0309038 A1    Oct. 29, 2015

Related U.S. Application Data

(60) Provisional application No. 61/728,817, filed on Nov. 21, 2012.

(51) Int. Cl.
*G01N 33/58* (2006.01)
*B01L 1/02* (2006.01)
(Continued)

(52) U.S. Cl.
CPC .............. *G01N 33/58* (2013.01); *B01L 1/025* (2013.01); *C07B 59/00* (2013.01); *C12M 41/14* (2013.01);
(Continued)

(58) Field of Classification Search
None
See application file for complete search history.

(56) References Cited

U.S. PATENT DOCUMENTS 3,613,308 A    10/1971   Klein et al.
5,324,636 A    6/1994    Bartos et al.
(Continued)

FOREIGN PATENT DOCUMENTS

CN    201894089 U  *  7/2011
DE    1773320 A1      12/1970
(Continued)

OTHER PUBLICATIONS

Charron et al., 2008, J. Amer. Soc. Hort. Sci. 133: 351-359.*
(Continued)

*Primary Examiner* — Amjad Abraham
*Assistant Examiner* — Bratislav Stankovic
(74) *Attorney, Agent, or Firm* — Marshall, Gerstein & Borun LLP

(57) ABSTRACT

The present invention relates to an isotope labeling chamber for labeling metabolites in an organism, comprising a reactor chamber (1) and an air regulation chamber (2), wherein the reactor chamber (1) comprises the following components: optionally, a housing frame (3), housing walls (4), at least one injection valve (5), where at least one housing wall (4) can be opened fully and/or in part and where at least one housing wall has a lock (6), and furthermore wherein the air regulation chamber (2) comprises the following components: a temperature-regulating unit (7), an air humidifica-
(Continued)

tion unit (8) and a gas absorption unit (9). Furthermore, the invention relates to a labeling method for plants in which the labeling chamber according to the invention is employed.

15 Claims, 12 Drawing Sheets

(51) Int. Cl.
*C07B 59/00* (2006.01)
*C12M 1/00* (2006.01)

(52) U.S. Cl.
CPC ..... *B01L 2300/069* (2013.01); *B01L 2300/10* (2013.01); *B01L 2300/12* (2013.01); *B01L 2300/18* (2013.01); *B01L 2400/06* (2013.01)

(56) References Cited

U.S. PATENT DOCUMENTS

| | | | |
|---|---|---|---|
| 5,352,414 A | 10/1994 | Rothenberg | |
| 5,848,591 A * | 12/1998 | Weismann | A61M 16/12 128/203.12 |
| 6,200,362 B1 | 3/2001 | Cecchi et al. | |
| 2010/0136675 A1 | 6/2010 | Heeg et al. | |

FOREIGN PATENT DOCUMENTS

| | | |
|---|---|---|
| DE | 1949001 A1 | 4/1971 |
| EP | 2 518 137 A1 | 10/2012 |

OTHER PUBLICATIONS

Berg et al., 1991, Agriculture, Ecosystems and Environment 34: 421-425.*
Zhou et al., 2002, SAE Technical Paper Series 2002-01-2280.*
Blank, L.M., et al., "Large-Scale 13C-Flux Analysis Reveals Mechanistic Principles of Metabolic Network Robustness to Null Mutations in Yeast." *Genome Biology* (2005), vol. 6, No. 6, R49, pp. 1-16.
Christensen, B., et al., "Metabolic Network Analysis of *Penicillium Chrysogenum* Using 13C-Labeled Glucose." *Biotechnology and Bioengineering* (2000), vol. 68, No. 6, pp. 652-659.
Fischer, E., et al., "Metabolic Flux Profiling of *Escherichia Coli* Mutants in Central Carbon Metabolism Using GC-MS." *European Journal of Biochemistry* (2003), vol. 270, No. 5, pp. 880-891.
Marx, A., et al., "Determination of the Fluxes in the Central Metabolism of *Corynebacterium Glutamicum* by Nuclear Magnetic Resonance Spectroscopy Combined with Metabolite Balancing." *Biotechnology and Bioengineering* (1996), vol. 49, No. 2, pp. 111-129.
Nöh, K., et al., Katharina, "The Benefits of Being Transient: Isotope-Based Metabolic Flux Analysis at the Short Time Scale." *Applied Microbiology and Biotechnology* (2011), vol. 91, No. 5, pp. 1247-1265.
Sauer, U., et al., "Metabolic Fluxes in Riboflavin-Producing *Bacillus Subtilis.*" *Nature Biotechnology* (1997), vol. 15, No. 5, pp. 448-452.
Schwender, J., et al., "Understanding Flux in Plant Metabolic Networks." *Current Opinion in Plant Biology* (2004), vol. 7, No. 3, pp. 309-317.
Sriram, G., et al., "Quantification of Compartmented Metabolic Fluxes in Developing Soybean Embryos by Employing Biosynthetically Directed Fractional 13C Labeling, Two-Dimensional [13C, 1 H] Nuclear Magnetic Resonance, and Comprehensive Isotopomer Balancing." *Plant Physiology* (2004), vol. 136, No. 2, pp. 3043-3057.
Szyperski, T, "13C-NMR, MS and Metabolic Flux Balancing in Biotechnology Research." *Quarterly Reviews of Biophysics* (1998), vol. 31, No. 1., pp. 41-106.
Van Dien, S.J., et al., "Quantification of Central Metabolic Fluxes in the Facultative Methylotroph *Methylobacterium extorquens* AM1 Using 13C-Label Tracing and Mass Spectrometry." *Biotechnology and Bioengineering* (2003), vol. 84, No. 1, pp. 45-66.
Yang, C., et al., "Metabolic Flux Analysis in Synechocystis Using Isotope Distribution from 13C-Labeled Glucose." Metabolic Engineering (2002), vol. 4, No. 3, pp. 202-216.
Zhao, J., et al., "Global Metabolic Response of *Escherichia Coli* to gnd or zwf Gene-Knockout, Based on 13C-Labeling Experiments and the Measurement of Enzyme Activities." *Applied Microbiology and Biotechnology* (2004), vol. 64, No. 1, pp. 91-98.
International Search Report in International Application No. PCT/EP2013/073245, dated Dec. 20, 2013.
European Search Report for European Application No. EP 12 19 3566, dated Apr. 12, 2013.

* cited by examiner 100 mm 100 mm 100 mm

METHOD AND DEVICE FOR MARKING ISOTOPES

CROSS-REFERENCE TO RELATED APPLICATIONS

This is the U.S. national phase of International Application No. PCT/EP2013/073245, filed Nov. 7, 2013, which claims the benefit of European Patent Application 12193566.2, filed Nov. 21, 2012 and U.S. Provisional Application No. 61/728,817, filed Nov. 21, 2012, each incorporated herein by reference in its entirety.

FIELD OF THE INVENTION

The present invention relates to an apparatus (isotope labeling chamber) for labeling organisms, preferably plants and animals, with isotopes and to a labeling method by using the apparatus according to the invention.

BACKGROUND OF THE INVENTION

Metabolic flux analyses (MFA) are becoming increasingly important as a central element of modern systems biology. Using MFA, the rates of metabolite movement within complex intracellular networks are quantified. In interaction with proteome, transcriptome and genome analyses, MFAs allow genetic and environmental effects on the growth of plants and other organisms to be demonstrated.

In the quantification of metabolic pathways via MFA, the labeling of compounds which are taken up by the plant has proved expedient (Szyperski (1998) $^{13}$C-NMR, MS and metabolic flux balancing in biotechnology research. Quart. Riev. Biophys. 31:41-106). Substances which are suitable in this context are radioisotopes such as, for example, $^{14}$C, $^{3}$H or $^{32}$P, or stable isotopes such as, for example $^{2}$H, $^{13}$C, $^{18}$O, $^{15}$N. The labeled compounds which are taken up by the plant, for example labeled carbon dioxide, follow intracellular metabolic pathways, whereby the labeled isotopes are distributed and incorporated into the intracellular metabolites or metabolic end products of interest (for example protein, starch, lipid, cell wall). The labeling in metabolites or metabolic end products can subsequently be detected via mass spectrometry or nuclear magnetic resonance. The typical labeling patterns of intermediates of the central metabolism or its end products, therefore, generate an "isotope fingerprint", by means of which the actual flux distribution may be calculated.

The experimental determination of systemic metabolic fluxes using $^{13}$C isotopes has long been used for studying a variety of organisms such as, for example, *Penicillium chrysogenum* (Christensen and Nielsen, 2000), *Escherichia coli* (Fischer and Sauer, 2003; Zhao et al., 2004), various yeasts (Blank et al., 2005), *Bacillus subtilis* (Sauer et al., 1997), *Corynebacterium glutamicum* (Marx et al., 1996), Synechocystis (Yang et al., 2002), *Methylobacterium extorquens* (Van Dien et al., 2003), soybean embryos (Sriram et al., 2004) and oilseed rape embryos (Schwender et al., 2004).

In contrast to traditional $^{13}$C labeling methods, the isotopic non-stationary metabolic flux analysis ("INST $^{13}$C-MFA"), also referred to as dynamic metabolic flux analysis, generates time profiles of the labeling patterns. Here, the transient labeling information of the metabolites is used for determining the in-vivo fluxes (for an overview, see Nöh and Wiechert, 2011, Appl. Microbiol. Biotechnol., 91, pages 1247-1265), which is not possible when using stationary methods, in which only the post-saturation $^{13}$C accumulation is measured. The dynamic method permits the metabolic flux analysis of photoautotrophic systems under physiological conditions with the use of $CO_2$. This analysis is not possible with stationary methods, for which reason in-vitro organ cultures are generally used for metabolic flux analyses of plants. In-vitro organ cultures are highly artificial systems, therefore the analysis of an intact plant under physiological conditions is advantageous.

Processes and apparatuses which are optionally suitable for isotope labeling are known from the prior art. For example, DE1949001 describes an apparatus for adjusting the atmospheric humidity in a plant growth chamber. A shortcoming of this type of arrangement is the necessity of an artificial light source since nontransparent material is used for the walls of the housing. Furthermore, the apparatus disclosed in DE1949001 lacks a material for absorbing carbon dioxide before the labeling is taken up, and also suitable devices for supplying $CO_2$.

An apparatus for regulating and determining the carbon dioxide content of a growth chamber by means of a regulated supply and removal of carbon dioxide and an apparatus for absorbing carbon dioxide are described in DE 1773320; however, the chamber described in DE 1773320 takes the form of a system for recording the total carbon dioxide turnover of plants (or other organisms such as lichen)—an intervention in the sense of continuous sampling, as required for the analysis of metabolic fluxes and made possible by the labeling chamber which is provided in accordance with the invention with a lock is not provided.

The technological background of the present invention is furthermore described in U.S. Pat. No. 3,673,733, where, likewise, the previous removal of nonlabeled carbon dioxide by means of the apparatus described in U.S. Pat. No. 3,673,733 is not possible.

U.S. Pat. No. 5,341,595 discloses a chamber for analyzing the growth of plants, where, likewise, the previous removal of nonlabeled carbon dioxide by means of the apparatus described in U.S. Pat. No. 5,341,595 is not possible. Moreover, the apparatus disclosed in U.S. Pat. No. 5,341,595 lacks a system for uniform aeration.

Chen et al. (Proteome Science 2011, 9:9 http://www.proteomesci.com/content/9/1/9) discloses a sealed plant growth chamber by means of which humidity, pressure, temperature and $^{13}CO_2$ concentration can be controlled and kept constant. In contrast to the present invention, the chamber described by Chen et al., however, does not include a lock which, in a dynamic MFA, would allow the continuous sampling without a gas exchange between the inside of the chamber and the external environment taking place.

This is the reason why, in Chen et al., the plants are maintained for several weeks in a pure $^{13}CO_2$ atmosphere, whereby they are almost completely $^{13}CO_2$-labeled. Thereafter, the chamber is opened and aired in a surge-like manner, whereupon samples are taken promptly. In other words, what is measured is not, as is possible in the chamber according to the invention, an accumulation of $^{13}$C in the plants/metabolites, but a depletion of the $^{13}$C, or an accumulation of the $^{12}$C from the surrounding atmosphere. Therefore, the method described by Chen et al. is considerably more costly since an inordinately higher amount of $^{13}CO_2$ is required.

Moreover, the process described in Chen et al. is a much greater deviation from natural/physiological conditions than the exposure of the plants to be labeled with $^{13}CO_2$ in the process according to the invention, which exposure is only short since the plants remain for a prolonged period in a sealed system in which an artificial atmosphere prevails. It is known that the photosynthetic utilization, by plants, of $^{12}CO_2$ and $^{13}CO_2$ differs.

Plant growth chambers which are suitable in principle for the $^{13}CO_2$ labeling of plants are supplied commercially under the product name "BioBox" by GMS Gaswechsel-Messsysteme GmbH Berlin; here, again, artificial illumination is employed, and only the costly variant of labeling up to the $^{13}CO_2$ saturation followed by measuring the $^{13}CO_2$ decrease in the various metabolites is possible. Here, too, the plants to be labeled have to remain in an artificial atmosphere and under artificial illumination conditions over a substantial period.

The direct measurement of the incorporation of $^{13}C$ as per the INST-C-MFA method is known from the prior art for single-celled organisms or liquid cultures of plant cells. Thus, for example, Young et al. (2011, Metabolic Engineering 13, pages 656-665) show a carbon flux chart of the single-celled cyanobacterium Synechocystis where the intracellular $^{13}C$ distributions were used for calculating metabolic fluxes under photoautotrophic conditions. The high sampling frequency required herefor may be attained for example by withdrawing a sample volume by means of a stopcock, if using liquid cultures.

An apparatus for rapid sampling and therefore measuring of the $^{13}CO_2$ incorporation of higher plants, which apparatus would make possible a considerably more efficient, more precise and more natural experimental set-up, is not known from the prior art.

Accordingly, it has so far not been possible to carry out such measurements in particular on intact crop plants such as maize, rice, soybeans or oilseed rape.

An object of the present invention was therefore to provide a labeling chamber for plants, by means of which labeling chamber reliable dynamic metabolic flux analyses may be carried out in plants without an undesired gas exchange between the inside of the chamber and the environment affecting the results measured. The prior-art systems do not allow any continuous sampling without adversely affecting the climate of the chamber in the long term. In addition, the prolonged $^{13}CO_2$ saturation achieved in the known systems does not correspond to the natural state. Moreover, less $^{13}CO_2$ is consumed (thus resulting in lower costs) in the apparatus according to the invention than in the inverse method described by Chen et al.

This object was achieved by the subject matter of the present invention, which relates to an isotope labeling chamber for labeling metabolites in an organism, preferably in a plant, comprising a reactor chamber (1) and an air regulation chamber (2), wherein the reactor chamber (1) comprises the following components:

optionally, a housing frame (3), housing walls (4), at least one injection valve (5), where at least one housing wall (4) can be opened fully and/or in part and where at least one housing wall has a lock (6), and furthermore wherein the air regulation chamber (2) comprises the following components:

a temperature-regulating unit (7), an air humidification unit (8) and a gas absorption unit (9).

The temperature-regulating unit, the air humidification unit and the gas absorption unit are connected to the upper reactor chamber in each case via passages and/or tubes and, therefore, together with the reactor chamber constitute circulations and air/gas exchanges which are independent of each other.

The reactor chamber (upper compartment: housing walls and upper part of the frame) is made as a module, in other words may be varied, only the air regulation chamber (lower compartment) being permanently provided with technology so that reactor or plant chambers of different sizes may be combined with the air regulation chamber.

M0: $^{12}C$-mass isotopomer of the analyte
M1: singly $^{13}C$-labeled mass isotopomer of the analyte (M1=M0+1)
M2: doubly $^{13}C$-labeled mass isotopomer of the analyte (M2=M0+2)
M3: triply $^{13}C$-labeled mass isotopomer of the analyte (M3=M0+3)

DESCRIPTION OF THE PREFERRED EMBODIMENTS (1) Isotope Labeling Chamber According to the Invention Reference is made to the drawings, in which identical components are referred to by identical numbers.

Figure 1:
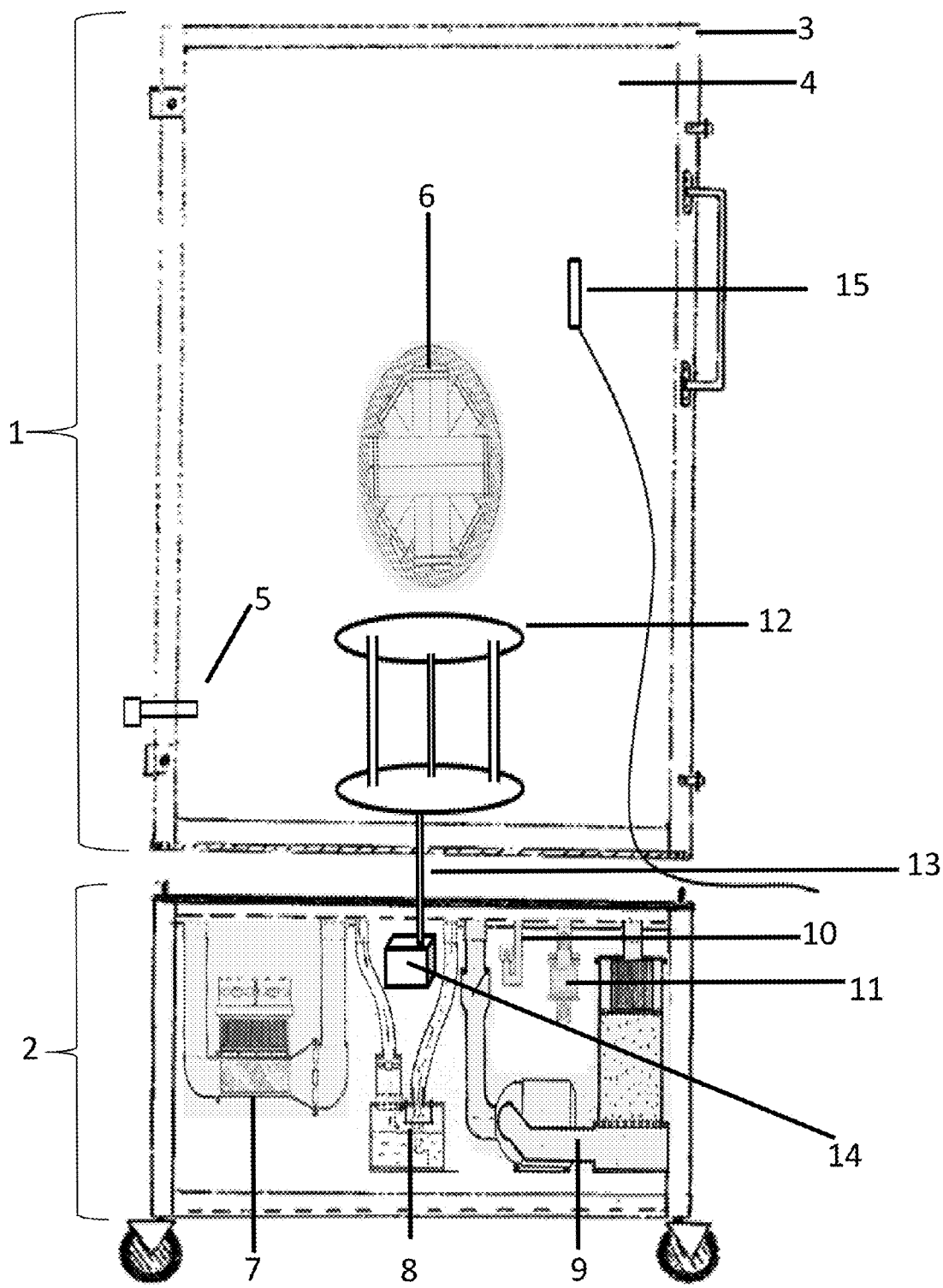
FIG. 1 shows an overall view of the labeling chamber according to the invention, where the numbers have the following meanings:
(1) Reactor chamber
(2) Air regulation chamber
(3) Frame
(4) Housing wall
(5) Injection valve
(6) Lock
(7) Temperature regulating unit
(8) Air humidification unit
(9) Gas absorption unit
(10) Pressure relief valve
(11) Suction relief valve
(12) Platform
(13) Drive shaft for the platform
(14) Motor for the platform
(15) $CO_2$ sensor

With reference first to FIG. 1 (dynamic isotope labeling chamber), the chamber according to the invention comprises a reactor chamber (1), and an air regulating chamber (2), wherein the reactor chamber (1) comprises the following components:

optionally, a housing frame (3), housing walls (4), at least one injection valve (5), where at least one housing wall (4) can be opened fully and/or in part and where at least one housing wall has a lock (6), and furthermore wherein the air regulating chamber (2) comprises the following components:

a temperature-regulating unit (7), an air humidification unit (8) and a gas absorption unit (9).

In the chamber there is typically arranged a platform (12), preferably a shelf, on which the plants to be analyzed are placed.

In a preferred embodiment, the shelf consists of plastic, especially preferably of polyvinyl chloride, and is designed as a rotatable plate which can be rotated by a geared motor (14) which can be controlled externally so as to position the plants within reach of the lock, within the chamber, whereby the sampling frequency which is possible is additionally increased. In a preferred embodiment, the motor may be located outside the plant chamber by using a shaft which penetrates the chamber wall and which is provided with radial packing rings ("shaft seals") so as to avoid an undesired gas exchange.

The size of the chamber should be selected such that it is suitable for labeling plants of different sizes. Preferably, the size of the chamber is selected such that it is suitable for labeling different developmental stages of crop plants such as, for example, maize, soybeans, rice, oilseed rape, cotton, wheat, rye, barley, triticale, millet and sorghum, hops, potatoes, tobacco, tomato, aubergine, pepper, linseed, flax, sunflowers, peas, and various bushes such as coffee, cocoa, tea, grasses and model plants such as *Arabidopsis thaliana*.

In this context, the plants to be labeled may either be wild forms or else various cultivars, hybrid varieties or transgenic plants in various developmental stages.

In a preferred embodiment, the labeling chamber is of modular design, composed of an air regulation chamber (as the lower part of the chamber) and a reactor chamber (as the upper part of the chamber), it being possible for the air regulation chamber to be combined, in principle, with reactor chambers of various sizes and types so as to make possible labeling experiments with different plants, developmental stages and regimes, such as number of plants, illumination conditions, effect of plant protectants agents or stress factors such as heat, low temperatures, dry conditions, salinity and the like.

In a preferred embodiment, the chamber is composed of reactor chamber and air regulation chamber with a height of 150-200 cm, a width of 50-90 cm and a depth of 50-90 cm and has a total volume of 600-1000 l. The reactor chamber on its own preferably has a height of 80-130 cm and has an overall volume of 450-800 l.

In an especially preferred embodiment, the reactor chamber has a width of 75 cm, a depth of 75 cm and a height of 110 cm and has a volume of approximately 560 l.

Figure 5:
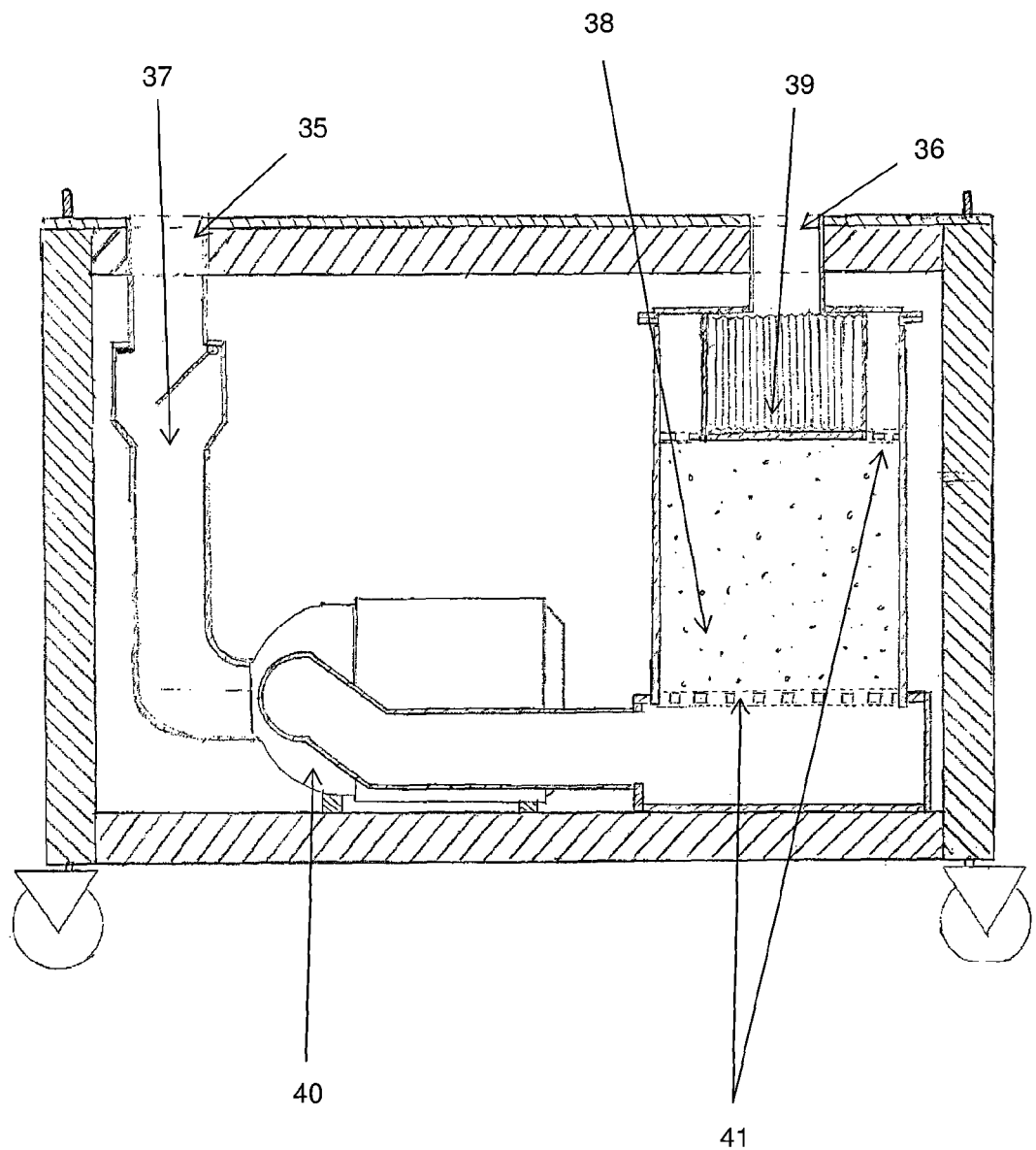
FIG. 5 shows the gas absorption unit (A) and the pressure compensation unit (B), where the numbers have the following meanings:
(A): (35) intake port; (36) outlet port; (37) check valve; (38) absorbent material; (39) fine-dust filter; (40) pump; (41) perforated plate
(B): (10) pressure relief valve; (11) suction relief valve; (38) absorbent material, (39) fine-dust filter; (42) ball valves
Figure 5:
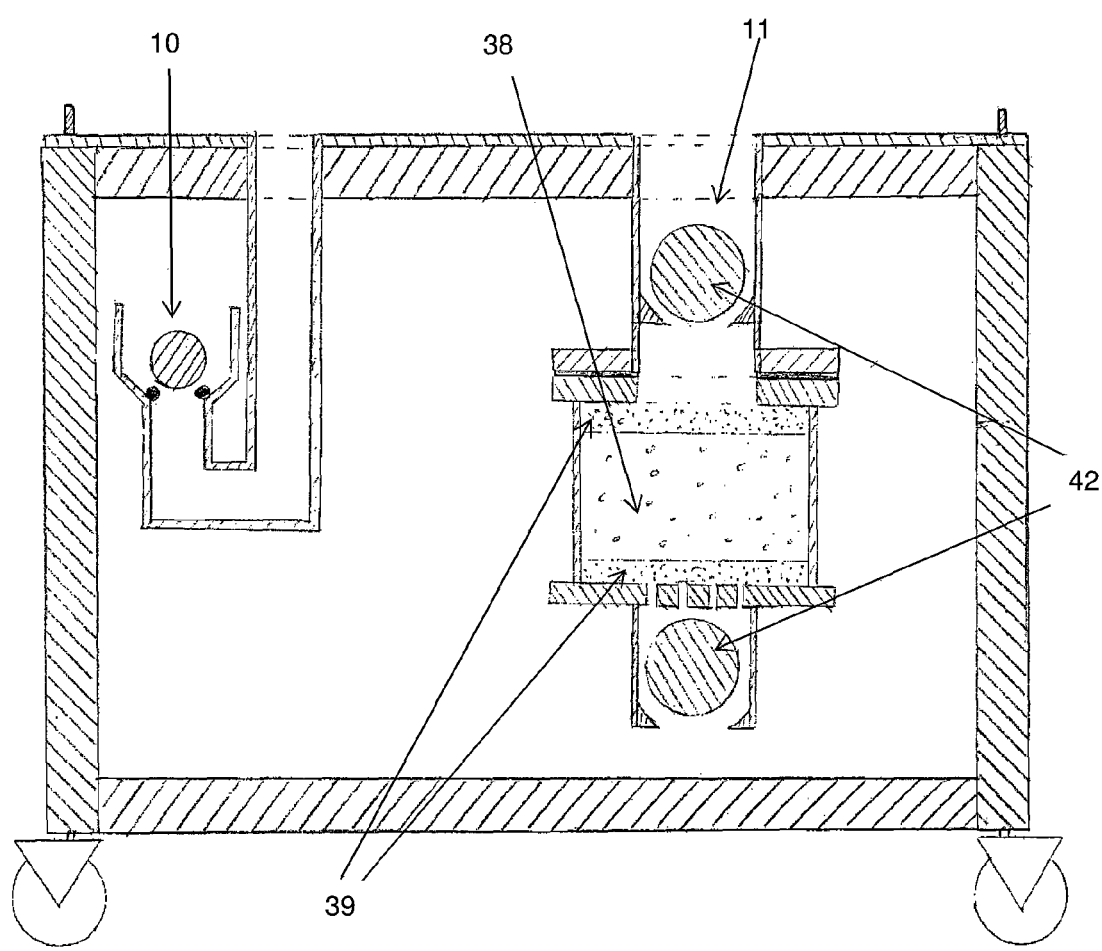

The housing wall (4) includes an injection valve (5) which is suitable for injecting $^{13}CO_2$. At a different or at the same housing wall (4) there may be located an outlet passage (see No. 35 in FIG. 5 (A)) which is connected to the gas absorption unit to which it removes nonlabeled carbon dioxide. The injection valve is furthermore suitable for introducing noxious gases, herbicides, other gaseous isotope labels, stable or radiolabeled gases (oxygen, CO, steam, nitrogen).

The at least one housing wall which can be opened fully and/or in part may take the form of a lid at the top of the reactor chamber or a door at one of the sides of the reactor chamber. Preferably, the housing wall which can be opened fully and/or in part is a door. "Which can be opened in full" means that the entire housing wall is attached in the form of a door; "which can be opened in part" means that an otherwise closed housing wall includes a smaller port in the form of a door.

A lock (6) in one of the housing walls allows continuous sampling for generating a dynamic measurement series because it prevents the ingression of nonlabeled carbon dioxide during the measurement series. The lock is preferably located in the door if the housing wall is one that can be opened in full. FIG. 2(A) to (F) shows various embodiments of the lock according to the invention. Typically, the lock comprises a frame, expandable elastic bands, a gasket, preferably made of foam rubber, and a cover which includes a magnet.

In a preferred embodiment, it is possible directly to reach through such a lock (for example for sampling purposes) without a gas exchange between the chamber and the environment actually taking place and without it being necessary first to open the lock by additional operations, which makes possible the sampling rhythm, of 2-10 seconds required for recording the transient metabolites. It is especially preferred that such a lock is composed of a multiplicity of elastic bands which overlap in the shape of a cross or star (see FIGS. 2(B) and (D)) which bands are stretched across the port in the housing wall.

Suitable materials for the expandable elastic bands are, for example, nitrile, natural rubber or others. In a preferred embodiment, the expandable elastic bands are composed of latex.

In an especially preferred embodiment, two or more of such locks may be arranged one behind the other, where an air curtain/stream of protective gas between the individual locks can ensure that the gas exchange is virtually completely prevented.

In a further embodiment, the chamber according to the invention comprises two separate locks through which for example a person may perform manipulations in the chamber with both hands, or else two persons may simultaneously or alternatingly take samples, whereby, for example, samples from different plant structures (such as, for example, leaf and influorescence) may be taken simultaneously and the interval between two samplings can additionally be shortened further.

Figure 2:
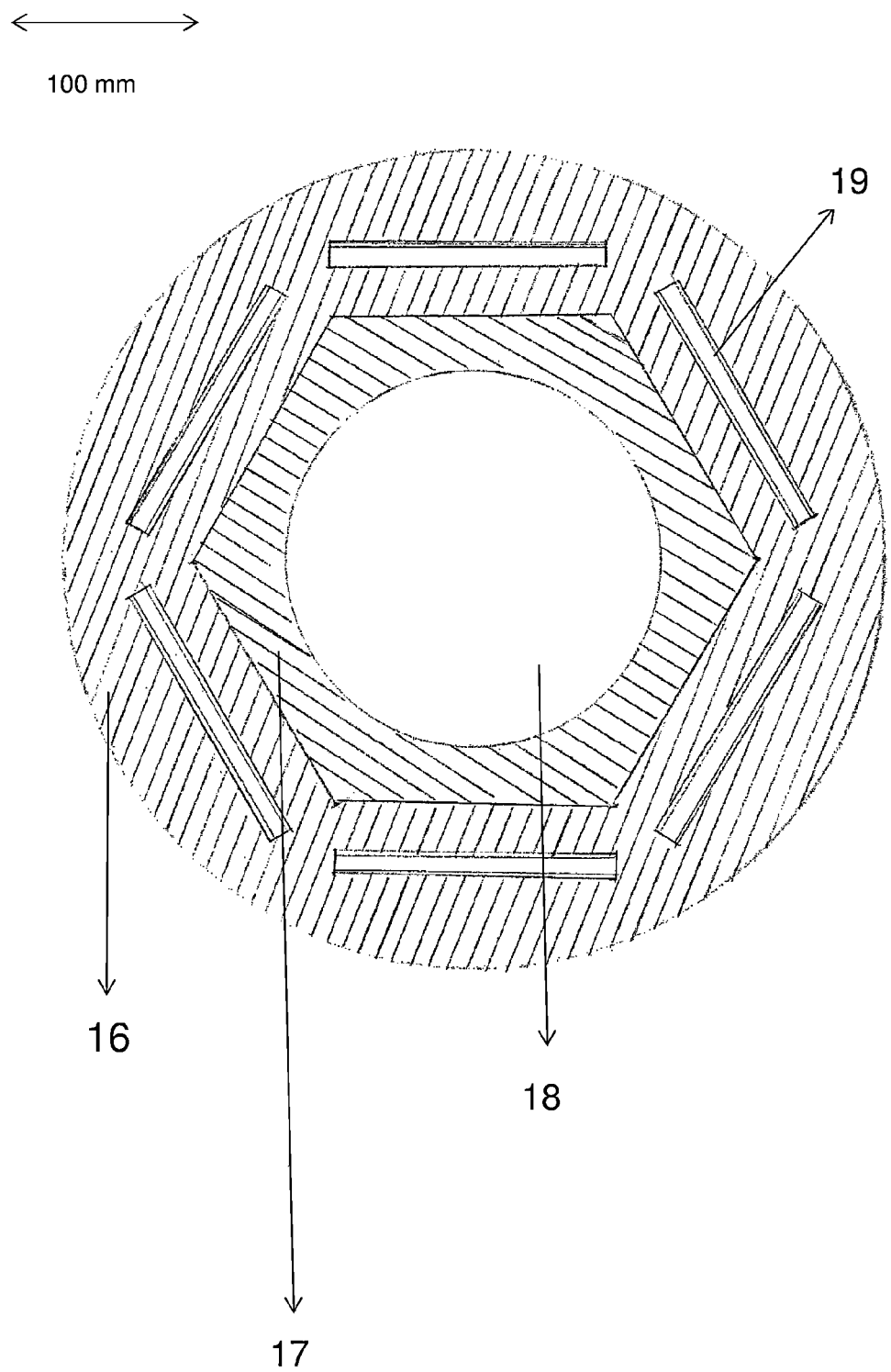
FIG. 2 shows a lock according to the invention, where the numbers have the following meanings: (A) construction of the lock of the chamber designed for six latex bands (open, without bands): (16) baseplate; (17) hexagonal plate for supporting the latex bands; (18) reach-through opening; (19) U-profile;
(B) lock of the chamber designed for six latex bands: (16) baseplate; (19) U-profile; (20) latex band;
(C) construction of the lock of the chamber designed for eight latex bands (open, without bands): (16) baseplate; (17) octagonal plate for supporting the latex bands; (18) reach-through opening; (19) U-profile;
(D) lock of the chamber designed for eight latex bands: (16) baseplate; (19) U-profile; (20) latex band;
(E) clamping mechanism for the latex bands: (16) baseplate; (17) hexagonal plate for supporting the latex bands; (18) reach-through opening; (19) U-profile; (20) latex band
(F) detailed view of the clamping mechanism: (19) U-profile; (20) latex band; (21) round bar; (22) foam rubber strip
Figure 2:
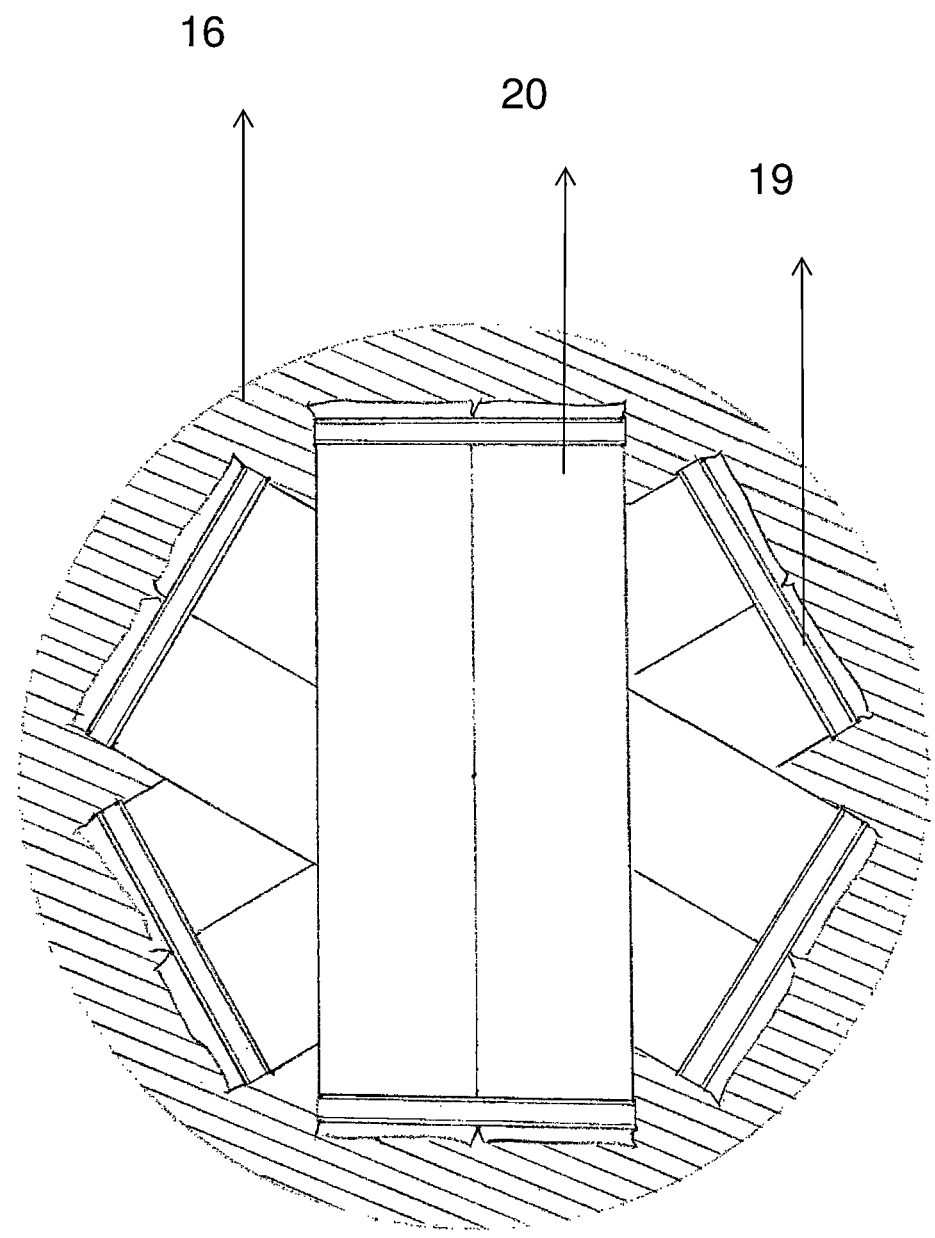
Figure 2:
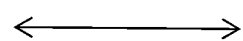
Figure 2C:
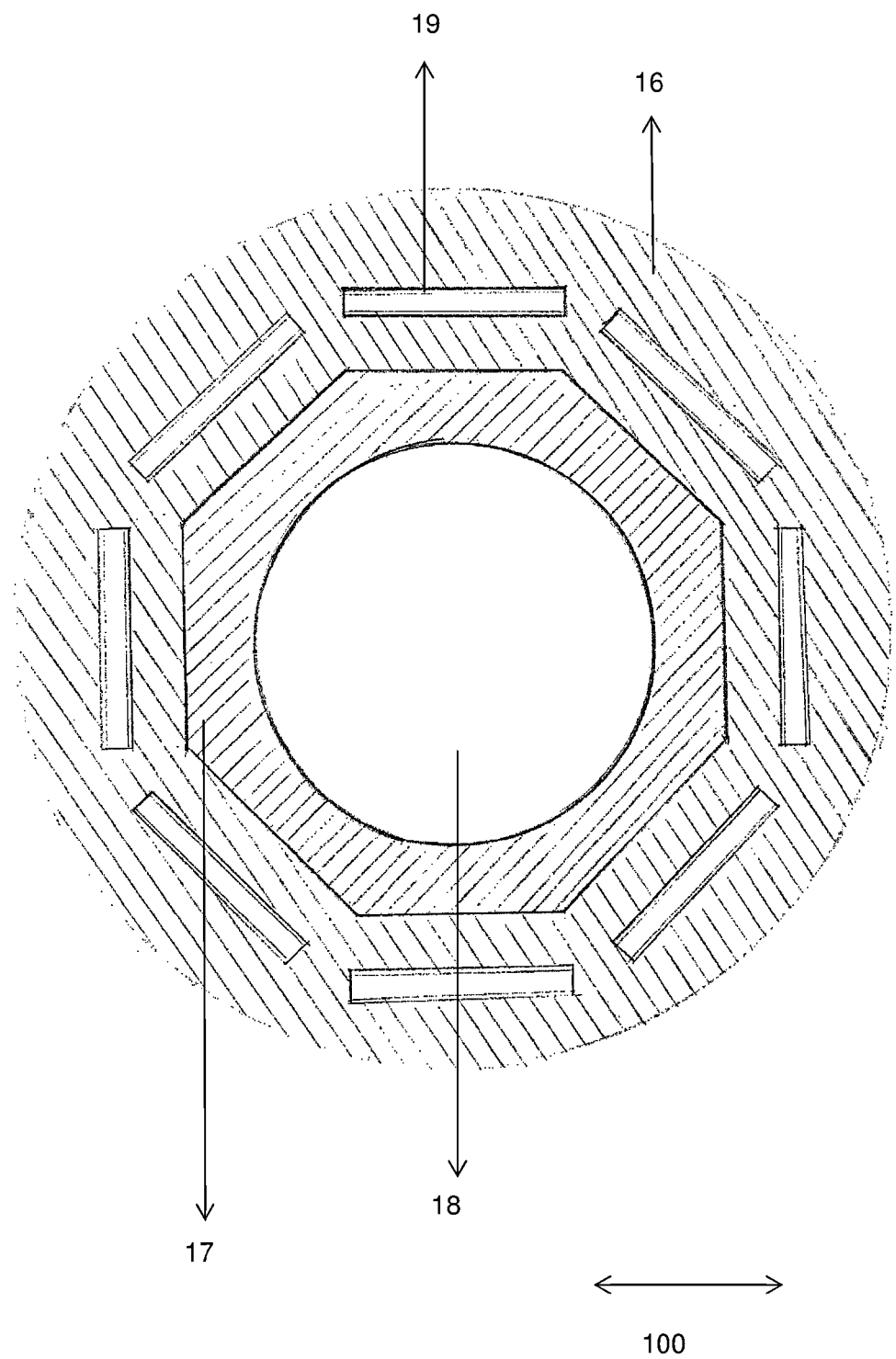
Figure 2:
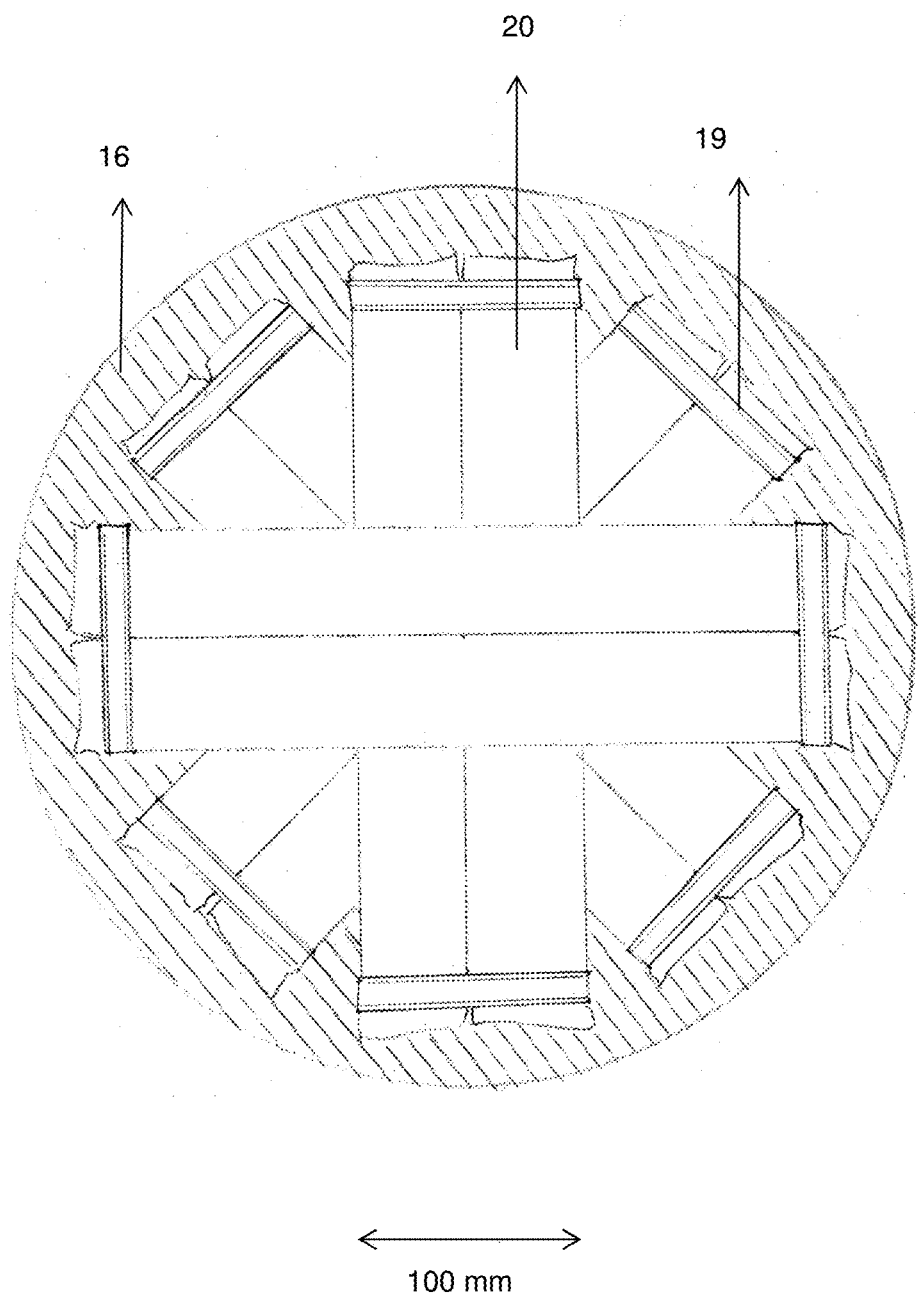
Figure 2:
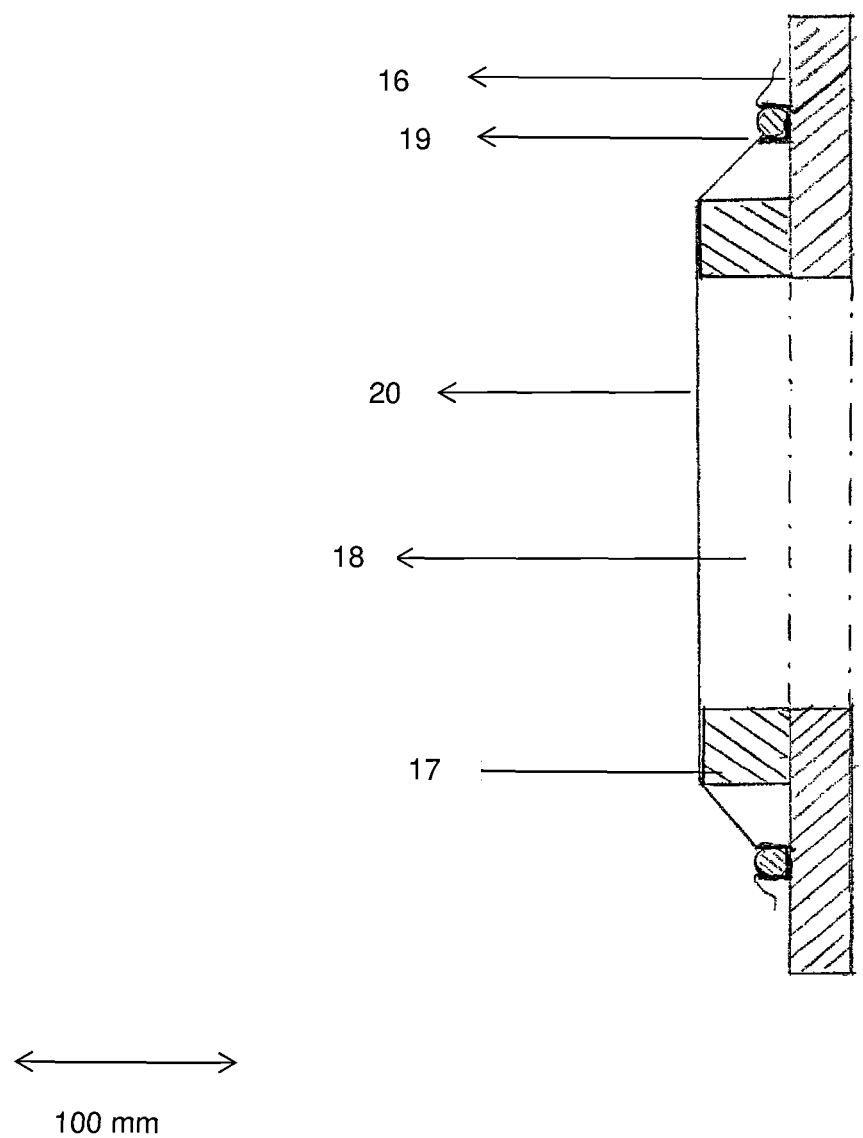
Figure 2:
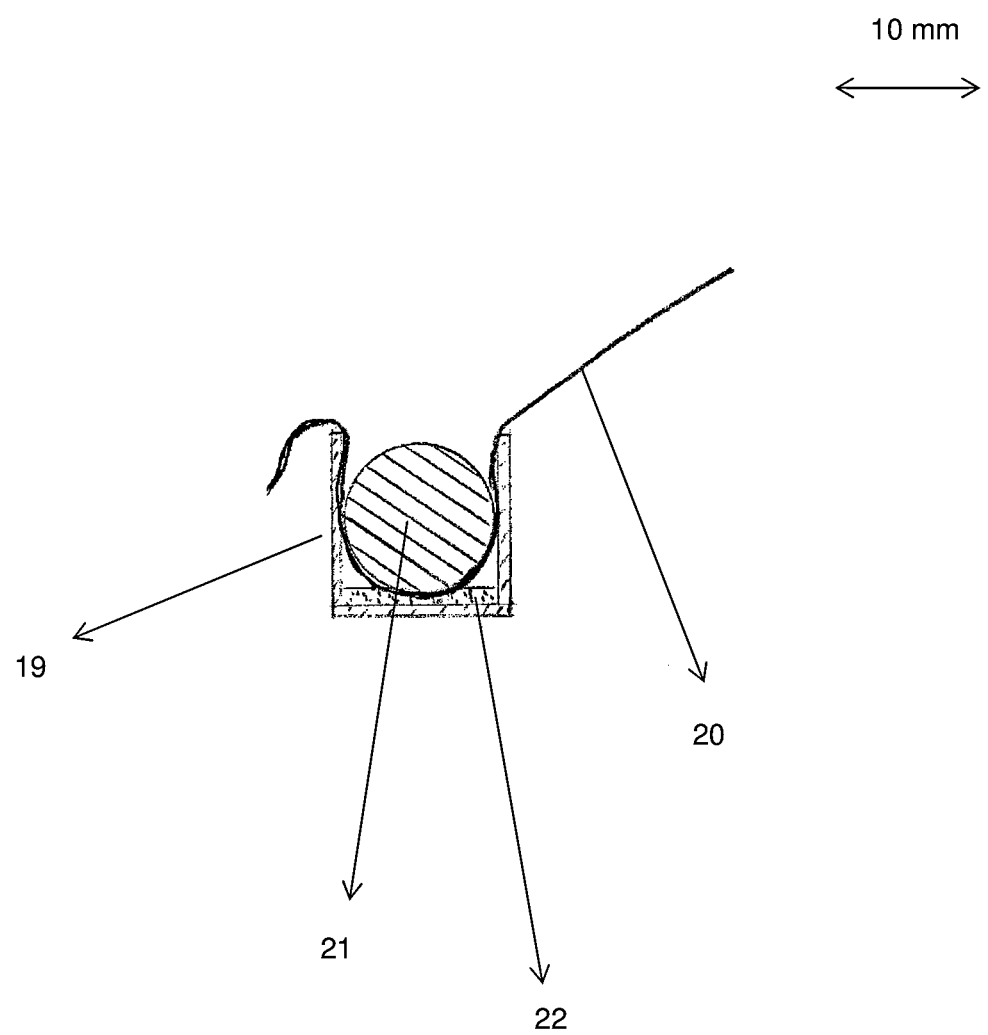

The lock preferably comprises at least two, especially preferably at least four, very especially preferably six or eight, expandable bands which overlap in the shape of a cross or star, which bands are preferably made of latex (see FIGS. 2(B) and (D)) and which ideally have a roughened surface, or as low as possible a coefficient of friction, so as to ensure that the hand and the samples proceed through the lock in an optimal fashion.

In an especially preferred embodiment, the latex bands are, by employing a clamping mechanism (see FIGS. 2(E) and 2(F)), stretched exchangeably onto a two-piece frame composed of a baseplate (16), equipped with a reach-through opening (18), for fastening the latex bands and a second, smaller plate, (hexagonal or octagonal; (17)), likewise equipped with a reach-through opening for supporting and aligning the latex bands.

To completely seal (and pressure-seal) the chamber between experiments, during the gas exchange or in experimental set-ups which do not require repeated sampling at short intervals, a cover of the port protected by the lock is advantageous. Such a cover may be effected for example by using a plate which may consist of the same material as the housing walls of the chamber, which may include a retaining facility and which can be fastened to the housing wall via a fastening facility, for example, screws, profiles, a plug facility or a magnet, so that the lock is sealed tightly.

In a preferred embodiment, the cover of the lock is composed of polycarbonate, is provided with a holding grip and is to be attached to the frame of the lock by magnets.

The housing walls are preferably composed of transparent materials which have high transparency while modifying as little as possible the spectral composition of the light which enters. This allows the use of artificial light sources to be avoided and the illumination conditions within the chamber to be adapted to different experimental conditions. Suitable materials are, for example, glass and synthetic materials such as acrylic glass or polyvinyl chloride and polycarbonate. The housing walls are preferably composed of polycarbonate.

The thickness of the individual housing walls may be different.

In a preferred embodiment, the housing walls have a thickness of 3 to 11, especially 5 to 9, mm.

To ensure simple handling of the chamber, the use of light materials is preferred. Materials which are suitable for the housing frame are a variety of materials such as, for example, timber, synthetic materials, without or with admixed wood fibers, metals such as stainless steel, in particular various aluminum alloys. In an especially preferred embodiment, the housing frame is composed of aluminum, preferably duraluminum.

If reliable data are to be obtained, it is essential, as already described hereinabove, that the air exchange between the chamber and the external environment is as little as possible, or nil. It is, therefore, expedient to additionally provide the housing frame with a sealant which makes possible an airtight sealing of the chamber. Suitable sealants are, for example (neoprene), acrylic or silicone, where materials with a low solvent content are to be preferred. In a preferred embodiment, the sealant is composed of acetic-crosslinking silicone without (fungicidal) admixtures (also known as aquarium silicone).

Various solutions such as, for example, rubber profiles or foam cushions, cellular rubber, are suitable for making possible an airtight sealing of the door and the cover of the lock. It is preferred to seal the door and the cover by means of frames made of closed-celled foam such as neoprene foam rubber, which frame is arranged on the housing.

Again, various solutions such as, for example, rubber profiles or foam cushions, cellular rubber, are suitable for placing the reactor chamber, that is to say the upper module of the preferred embodiment of the chamber, on the air regulation chamber, that is to say the lower module of the chamber, in an airtight manner.

It is preferred to connect the reactor chamber, that is to say the upper module of the preferred embodiment of the chamber, to the air regulation chamber, that is to say the lower module of the chamber, in an airtight manner by applying a surrounding neoprene foam rubber strip between the two modules. In an especially preferred embodiment, the upper module of the chamber is held in position by four spigot bolts, with a surrounding neoprene foam rubber strip ensuring an airtight connection of the two chamber modules.

The plant material to be analyzed should be exposed to controlled environmental conditions such as temperature, humidity, pressure and air supply, during the experiment. To this end, the air regulation chamber (2) which comprises a temperature-regulating unit with aeration facility (7), an air humidification unit (8) and a gas absorption unit (9), is preferably located underneath the reactor chamber (1).

Figure 3:
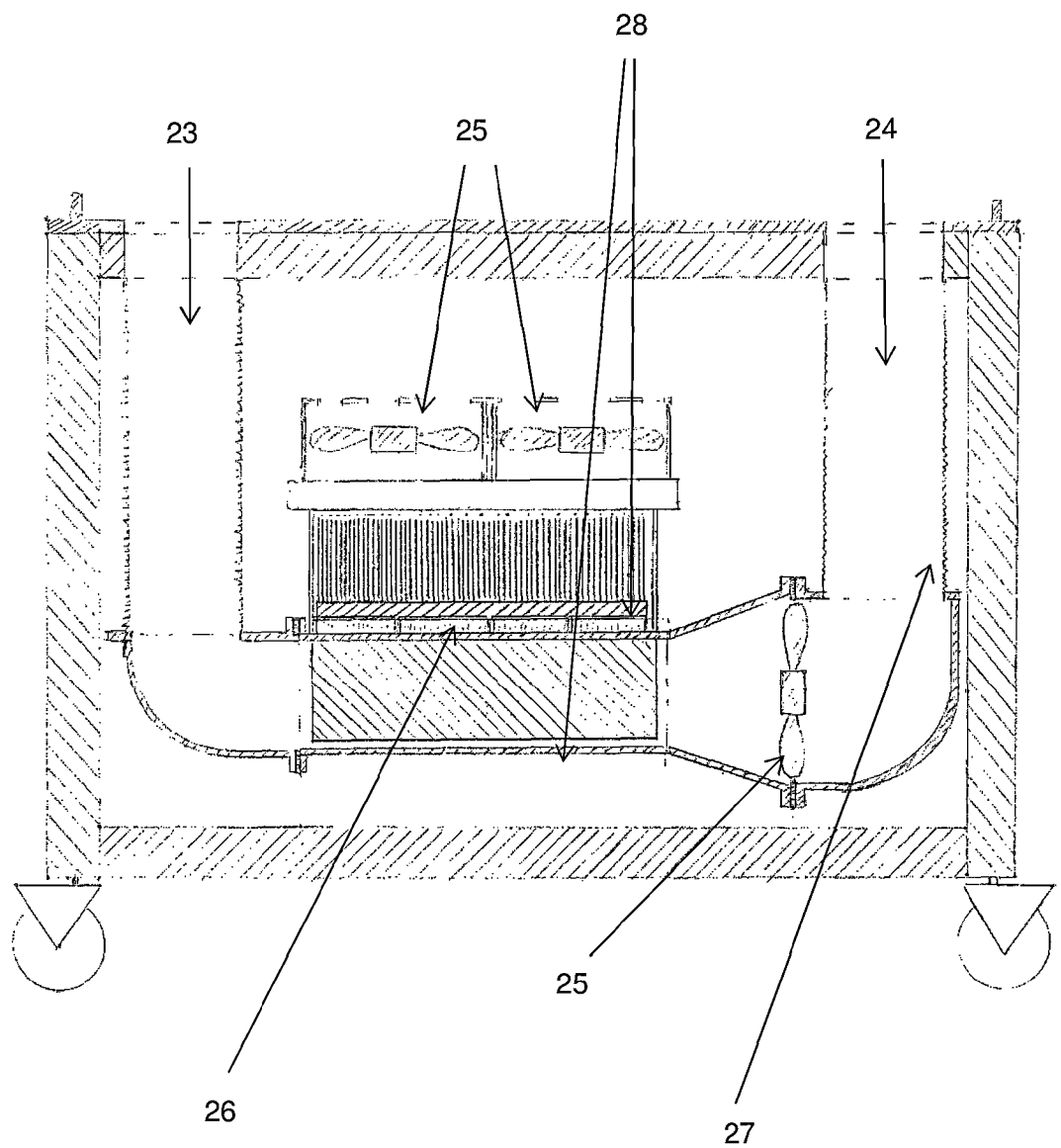
FIG. 3 shows a schematic representation of the temperature-regulating unit with ventilation unit, where the numbers have the following meanings:
(23) air/outlet pipe; (24) air/suction pipe; (25) fan/blower; (26) Peltier elements for heating/cooling; (27) flexible ventilation pipe made of aluminum; (28) ribbed heat sink made of aluminum

Located in the temperature regulating unit with aeration facility (FIG. 3) is at least one fan or blower, preferably two fans/blowers. The stream of circulating air depends on the volume of the labeling chamber and is intended to make possible an efficient mixing of the gases. The aim here is a moderate ("gentle") air movement within the chamber combined with a high throughput of air, which can preferably be achieved by relatively enlarging the ports of the circulating-air passage and the use of a plurality of blowers.

In a preferred embodiment, the stream of circulating air amounts to approximately 1000 l of air per minute.

For regulating the temperature, a Peltier element together with a cooling facility, in a preferred embodiment with an aluminum ribbed heat sink with one or more blowers, is located in the lower part of the housing. In an especially preferred embodiment, the Peltier element has a power consumption of 380 watts.

Figure 4:
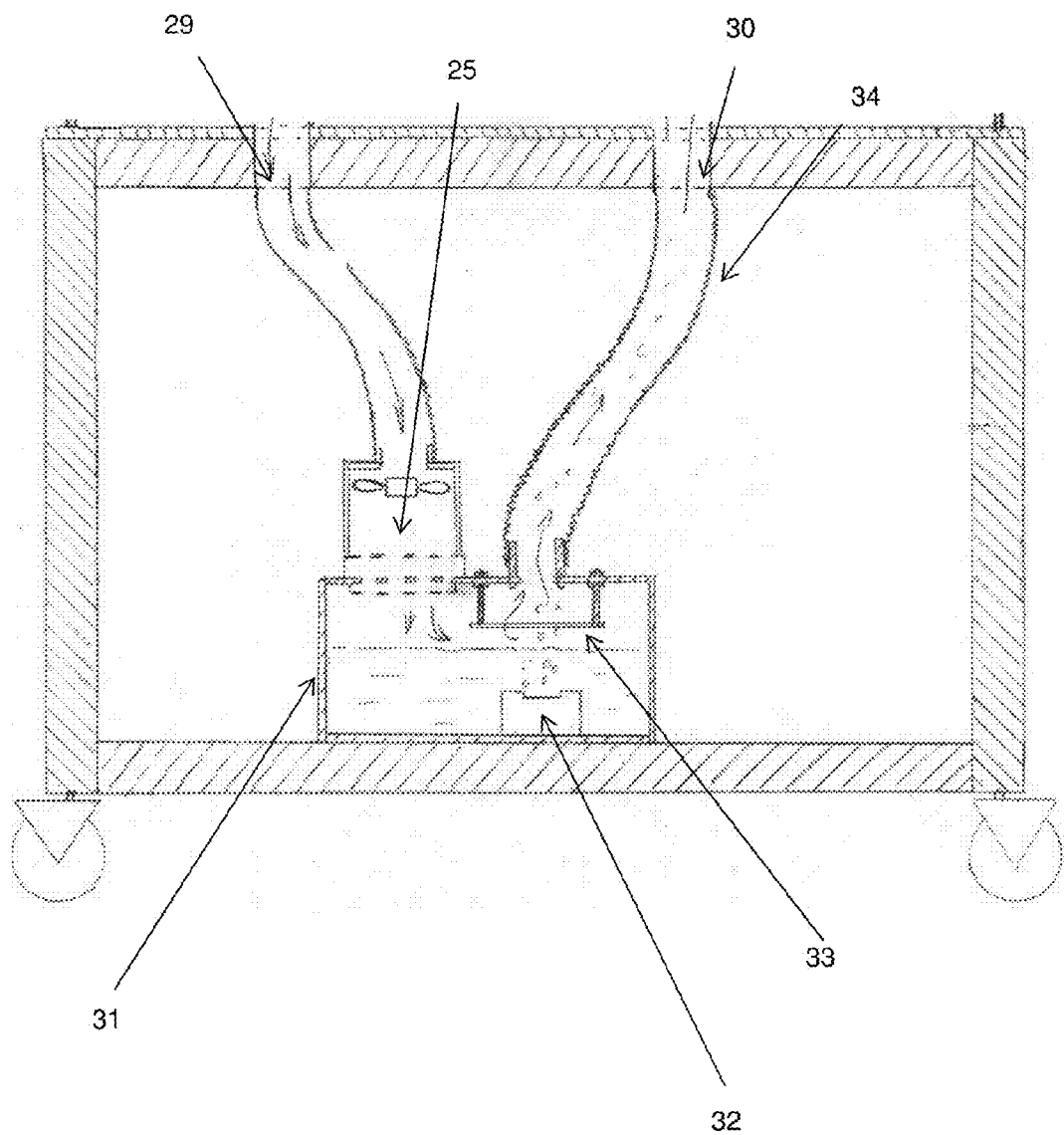
FIG. 4 shows a schematic representation of the air humidification unit, where the numbers have the following meanings:
(25) fan/blower; (29) air intake; (30) air outlet; (31) water container filled with water; (32) ultrasonic atomizer; (33) splash plate; (34) flexible plastic tube

The air humidification unit (FIG. 4) preferably comprises a water-filled water container in which there is located a (piezoceramic) ultrasonic transducer. In order to be able to exploit ultrasonic waves for the humidification of air, electrical energy must be converted into mechanical energy. This is done in the piezoelectrical transducer. Piezoceramic ultrasonic transducers are known from the prior art (see, for example: AIRWIN). An advantageous frequency of the ultrasonic transducer for efficiently nebulizing water and thus humidifying the introduced air is a frequency of, for example, 2 MHz. As shown in FIG. 4, the air humidification unit is connected to the reactor chamber via tubes for the intake and outlet of air.

As described hereinabove, an error-free experimental set-up requires that unlabeled carbon dioxide which is present in the chamber atmosphere is removed as completely as possible from the chamber and bound so that the plant material to be analyzed can predominantly take up labeled $^{13}CO_2$ and incorporate this $^{13}CO_2$ into the metabolism in a measurable manner.

Accordingly, the gas absorption unit (see FIG. 5A) preferably comprises a material capable of absorbing carbon dioxide, especially preferably a mixture of NaOH/KOH and CaOH (also known as soda lime). Various compositions of such carbon dioxide absorbers are known from the prior art. As a rule, the absorbent material (38) has added to it an indicator which visualizes the $^{13}CO_2$ saturation/the state of consumption of the absorbent material by means of a color change.

In an especially preferred embodiment, the absorbent material is soda lime. In a preferred embodiment, approximately 15 l of absorbent material (38) are employed. The purified air is preferably passed through a fine-dust filter (39) after having passed through the absorbent material.

In a preferred embodiment, the pump which sucks the air from the chamber via the suction port and passes it over the absorbent material has a power suitable for a throughput of between 1000 and 3000, especially preferably controllable between 1800 and 2500, liters of air per minute. In an especially preferred embodiment, the pump is a centrifugal pump which can be controlled for an air throughput of either 1800 or 2500 l/min.

To avoid a subatmospheric pressure during the exchange process (see FIG. 5(B)), an inlet port (=vacuum valve, see FIG. 5(B), right-hand side), or No. (11) in FIG. 1), which is likewise provided with a fine-dust filter (39) and a $CO_2$ absorbent (38) is located in the bottom of the labeling chamber, so that the air which streams in from the surroundings of the reactor chamber as a result of the subatmospheric pressure is stripped of its $CO_2$. The compensation of a superatmospheric pressure, which is established briefly after switching off the pump towards the gas absorption unit is effected via a ball valve (pressure-relief valve; FIG. 5(B), left-hand side, or No. (10) in FIG. 1), through which air can stream out of the reactor chamber, but no air may enter the reactor chamber. This combination of inlet port/vacuum valve with $CO_2$ absorbent and outlet ball valve/pressure-relief valve allows the labeling experiments to be carried out under pressure conditions which correspond largely to those of the environment ("standard pressure").

So as to be able to control as uniformly as possible a $^{13}CO_2$ content, the labeling chamber according to the invention additionally includes a facility for measuring carbon dioxide. Suitable for this purpose are various source receivers known from the prior art, for example infrared sensors, photoacoustic sensors or mass spectrometers. The $^{12}C$ concentrations and the $^{13}C$ concentrations can preferably be determined/delimited from each other separately.

In a preferred embodiment, the $CO_2$ measuring facility is a mass spectrometer by means of which separate readings for $^{12}CO_2$ and $^{13}CO_2$ can be determined.

In an especially preferred embodiment, the $CO_2$ measuring facility is a mass spectrometer for analyzing a mass range of from 1 to 100 amu (atomic mass units).

(2) The Labeling of Plants

The distributions of metabolic fluxes allow conclusions regarding metabolic reactions and bottlenecks in the metabolism of plants and are used as starting points for rational metabolic engineering and for a more in-depth analysis of the metabolism of plants. Using the method according to the invention, the metabolism of a plant may also be analyzed under stress conditions, for example after the treatment with a plant protectant, after the treatment with low temperatures, drought, salinity and the like. The effect of a genetic modification on the metabolism of the plant may furthermore also be analyzed.

The labeling experiments are preferably carried out under physiological, or natural, $CO_2$ concentrations. This entails a $^{13}CO_2$ concentration required of approximately 360 to 420, preferably approximately 380 to 400 ppm in the reactor. To this end, the natural $CO_2$ in the chamber must be removed as completely as possible before the experiment. To this end, the plants are first placed into the chamber and the doors sealed so that no air exchange with the environment may take place. It is preferred to use useful plants such as, for example, maize, soybeans, rice, oilseed rape, cotton, wheat, especially preferably maize or rice. The plants to be labeled may be in different developmental stages such as embryonal stage, vegetative stage or generative stage.

The plants are preferably in one of the following stages: germination/sprouting, leaf development, tillering, stem elongation, booting, ear/panicle emergence, flowering, fruit development, fruit or seed maturation, death or entering dormancy. The plants to be labeled are especially preferably in one of the following stages: leaf development, tillering, stem elongation, booting, ear/panicle emergence, flowering, fruit development, fruit or seed maturation.

In a preferred embodiment, several plants which are in the same developmental stage are labeled simultaneously.

In a further preferred embodiment, several plants which are in different developmental stages are labeled simultaneously.

In a further preferred embodiment, the plants to be labeled by the method according to the invention are transgenic plants.

In a preferred embodiment, at least 16 12-day-old rice seedlings are labeled simultaneously after germination by introducing them, together with their culture vessels, into the reactor chamber.

In a further embodiment, the plants are not only $^{13}C$-labeled, but also $^{15}N$-labeled, by placing them, within the reactor chamber, into a vessel for hydroponic cultures which comprises a $^{15}N$-labeled nutrient salt.

In a preferred embodiment, the plants are labeled simultaneously with $^{13}C$ and $^{15}N$, with the two labeling pulses being applied simultaneously.

Before the experiment, the $CO_2$ is removed via a $CO_2$ absorbent, preferably using lime soda. The $CO_2$ absorbent is placed outside and connected to the housing via the plastic tubes. The air from the upper part of the chamber is sucked by means of a pump and, simultaneously, after absorption has taken place, the $CO_2$-free air is provided to the lower chamber, directly towards the fan. The exchange takes place in less than 60 seconds, preferably less than 45 seconds, especially preferably less than 30 seconds. Directly thereafter, the respective amount of the $^{13}CO_2$ gas is injected via a syringe. By positioning the injection valve directly above the outlet port of the circulating-air passage, optimal mixing in the sense of the $^{13}CO_2$ being distributed uniformly into the volume of the reactor chamber, and thus the establishing of the desired $^{13}CO_2$ concentration, takes place.

According to the experimental set-up, sampling is started as simultaneously as possible with the switch-over of the chamber atmosphere to $^{13}CO_2$, or shortly thereafter, whereupon sampling takes place at regular intervals. Preferably, sampling takes place every 2 to 20 seconds, preferably every 2 to 10 seconds, especially preferably every 2 to 5 seconds, for at least the first 60 seconds. Preferably, further samplings take place at intervals of, for example, 2, 5, 10, 20, 30, 40, 50, 60, 70, 80, 90, 120, 180, 240, 300 seconds, where at least a period of 900 seconds from the first sampling is covered by regular samplings.

In a preferred embodiment, the first sample is taken simultaneously with the feeding of the $^{13}CO_2$. Further samples are taken in each case 10, 20, 30, 40, 50, 60, 90, 120, 150, 180, 240, 300, 420, 600, and 900 seconds after feeding the $^{13}CO_2$.

In a further embodiment, sampling may, however, also take place over a considerably longer period, for example a period of several hours, days or weeks.

Preferably, the process according to the invention is repeated more than once, especially preferably twice, three times or more frequently, for each experiment, with identical sampling intervals.

The remainder of the $^{13}CO_2$ in the chamber can be removed via the $CO_2$ absorbent before starting the next experiment.

The present invention is illustrated with reference to the following examples, without being limited thereto.

EXAMPLES

Example 1: General Procedure

A plant is labeled with one or more stable isotope labels in an isotope labeling chamber according to the invention. The distribution of the isotope label in the plant is analyzed in freeze-dried and ground plant material at different points in time after the labeling pulse. Sampling after the labeling pulse is done from the isotope labeling chamber according to the invention, using a lock, whereby a change in the atmosphere of the isotope labeling chamber according to the invention during sampling is prevented. The distribution of the label in a sample is analyzed by mass spectrometry following chemical extraction of the plant material. Fluxes in the metabolism of intact plants can be calculated on the basis of the label distribution, using mathematical modeling.

Example 2: Materials and Methods 2.1 Supplies for Carrying Out the Labeling Experiment
  Isotope labeling chamber according to the invention
  Gas-tight bags for transporting and storing $^{13}CO_2$
  Gas-tight syringe
  $^{13}CO_2$ in gas cylinder equipped with pressure-reducing regulator
  $^{15}NH_4NO_3$ (optional)
  Hydroponic system (trough with perforated polystyrene plate)
  Plant vessels
  Compost
  Plant substrate granules
  Plants
2.2 Supplies for Sampling and Comminution
  Scales
  Liquid nitrogen and suitable trough
  Harvesting containers (2 ml Eppendorff vials, Falcon Tubes in different sizes)
  Securing shears
  Securing tongs
  Tweezers
  Vibration grinding mill
  Grinding beaker with balls (diameter 2-15 mm)
  Freezer −80° C.
2.3 Supplies for the Extraction of Samples
  Fast Prep with dry-ice tray
  Dry ice
  Centrifugal filter
  Centrifuge
  Freeze-drying system
  Measuring vessels
  Eppendorff vessels
  Falcon vessels 2.4 Supplies for Measuring Samples
  UPLC
  Mass spectrometer
2.5 Chemicals
  Solvents (ethanol, acetonitrile, water, dichloromethane)
  Ammonium acetate
  Tributylammonium
  Acetic acid
  Internal standards
  Test substances Example 3: Analytical Procedure 3.1 Labeling Experiment The labeling experiment is carried out for determining metabolic fluxes in intact plants. The distributions of metabolic fluxes allow conclusions regarding the metabolic reaction and bottlenecks in the metabolism of plants and are used as starting points for rational metabolic engineering and for the in-depth analysis of the metabolism of plants. Using the method according to the invention, the metabolism of a plant may also be analyzed under stress conditions, for example after the treatment with a plant protectant, after the treatment with low temperatures, drought, salinity and the like. The effect of a genetic modification on the metabolism of the plant may furthermore also be analyzed. To study the fluxes in a plant, the latter is labeled with a stable isotope. The isotope label is monitored in the plant's metabolism. Based on the distribution of the label, conclusions may be drawn regarding the metabolism of the plant being studied. If a stress condition is to be analyzed, the stress condition may be applied at any point in time before or during the labeling experiment.

3.2 $^{13}CO_2$-Labeling of an Intact Plant

Plants in different developmental stages are placed into the isotope labeling chamber according to the invention. The transparent isotope labeling chamber is located somewhere suitable for the plant growth, for example a plant growth chamber, a greenhouse, in the open, and the like. This ensures a sufficient supply of light across the transparent wall of the chamber. The isotope labeling chamber according to the invention is sealed in an airtight manner against the external atmosphere. Humidity and temperature are set to match the requirements of the plant species studied (or the experiment). Before carrying out the labeling experiment, ambient $^{12}CO_2$ is removed from the air located in the chamber with the aid of an absorbent. Thereafter, the desired $^{13}CO_2$ concentration (for example 400 ppm) is established in the chamber. The air stream located in the chamber ensures a uniform distribution of the $^{13}CO_2$ in the chamber within a few seconds. The $^{13}CO_2$-incubation time is referred to as the labeling pulse. Typically, labeling pulses of between 2 seconds and 180 minutes are performed, but longer pulse experiments are also possible. After setting the atmosphere to $^{13}CO_2$, samples are taken from the chamber, or intact plants are harvested from the chamber (with only a minimal change in atmosphere in the chamber). In addition, it is possible after the labeling experiment to store plants in a regular environment and atmosphere (for example plant growth chamber, greenhouse and the like) for their further development and to harvest them only at a later point in time.

3.3 $^{15}N$-Labeling of Intact Plants

To apply an additional $^{15}N$-labeling pulse, plants are grown in a hydroponic system. The hydroponic system comprises a nutrient solution with a nitrogen source (for example $NH_4NO_3$). At the point in time of the experiment, the plants are transferred into a second hydroponic system in which the nitrogen source available (for example $NH_4NO_3$) has been replaced by $^{15}N$-comprising compounds (for example $^{15}NH_4^{15}NO_3$, $^{14}NH_4^{15}NO_3$, $^{15}NH_4^{14}NO_3$). After the labeling pulse has ended, the plants are removed from the hydroponic system, rinsed with regular nutrient solution and transferred, for their further development, into a regular hydroponic system which comprises nitrogen compounds in the form of $^{14}N$ nitrogen. Alternatively, plants are harvested directly after the labeling pulse. A $^{15}N$ labeling pulse may be applied in combination with the $^{13}CO_2$-labeling of the intact plant.

Example 4: Harvesting the Plants

Plants are harvested from the chamber during the labeling experiment. To this end, the chamber was fitted with a variable lock. In the chamber wall there is located a port onto which the frame of the lock according to the invention (with foam rubber seals) is placed tightly and secured with screws. The lock is composed of a frame with rubber bands which make possible the minimal reaching into the chamber from the outside (FIG. 2(A)-(F)). In the event that the lock is not used for a prolonged period, or if it is necessary to seal the chamber in a pressure-tight manner (for example for removing ambient $^{12}CO_2$), the lock can be sealed with a transparent cover. This cover is placed tightly on the lock by means of magnetic seals. Plant material is harvested according to the experimental design and immediately frozen in liquid nitrogen. The nitrogen container is located outside the chamber. Harvesting may be started as early as a few seconds after starting the labeling experiment. Harvesting is done using what is known as a cut-and-hold shears for roses. This tool takes the form of shears or tongs which cuts and simultaneously grips (or retains) the plant or plant parts. During harvesting, intact plants or various plant parts may be harvested separately and frozen (for example flag leaf, leaf, stem, ear, spikelet, seed, root, seedling). After harvesting, all plants/plant parts are stored at −80° C.

Example 5: Preparing the Samples 5.1 Comminuting the Samples

Frozen plant material is comminuted in a vibration grinding mill. Grinding beakers and grinding balls (diameter 2-15 mm) which are suitable for the plant material are used for this purpose.

Example

Seedling: 2 ml Eppendorf vial, 2 steel balls,
Root: 2 ml Eppendorf vial, 2 steel balls,
Leaf: 20 ml scintillation vessel in a stainless-steel grinding beaker, 5 steel balls,
Ears: Stainless-steel grinding beaker, 1 steel ball.

Comminuted plant material is stored in the freeze-dried state at room temperature under argon.

5.2 Extraction of the Samples (NRJ Method as Disclosed in WO2011/003945) with Minor Adaptations)

10 mg of dried plant material is weighed in and treated with 900 µl of a cold (−80° C.) dichloromethane/ethanol (2:1 v/v) solution. Thereafter, the suspension is overlaid with 150 µl of 1.5 M AmOAc, and the sample is extracted using a FastPrep (cooled with dry ice), using glass beads. After the first extraction (30 s FastPrep, 6.5 m/s), the sample is centrifuged at 14000 rpm and 0° C. for 2 min. Thereafter, 100 µl of the top phase are removed and transferred into centrifugal filters. Thereafter, 150 µl of 1.5 M AmOAc solution are added, and the material is extracted once more (30 s FastPrep (cryo with dry ice), 6.5 m/s). Following recentrifugation at 14000 rpm and 0° C., 200 µl of the top phase are combined with the first extract in the centrifugal filter and the mixture is centrifuged at 14000 rpm and 0° C. for 5 min. 240 µl of filtrate are transferred into measuring vessels and freeze-dried for two days. After the freeze-drying is complete, the samples are reconstituted in 100 µl of solvent A and analyzed by means of the NRJ method (ion-pair chromatography, UPLC-LC-MS/MS).

Example 6: Evaluation of the Isotope Ratios

Figure 6:
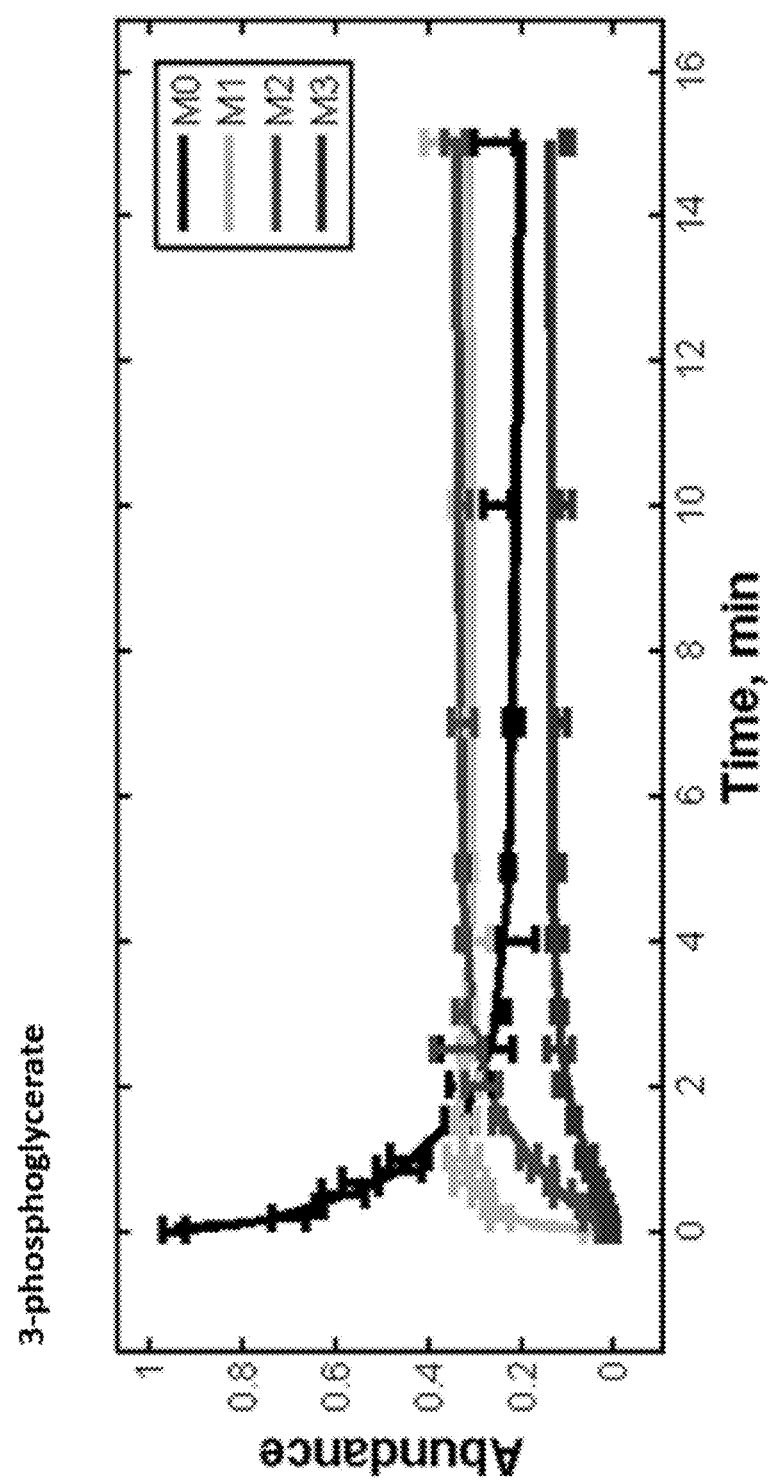
FIG. 6 shows the result of an LC-MS/MS measurement with reference to a central entry metabolite of the carbon dioxide metabolism, viz. 3-phosphoglycerate. The data shown are the relative frequencies of the various mass isotopomers as influenced by the increasing incorporation of $^{13}C$.

In the LC-MS/MS measurement (where LC-MS/MS stands for liquid chromatography—mass spectrometry/mass spectrometry), MRM transitions (where MRM represents "multiple reaction monitoring") are recorded for all isotopomers for all analytes. The areas or heights of the respective peaks which represent the individual isotopomers are determined by integration (FIG. 6).

The peak areas of the isotopomers are plotted as a function of the sampling time. As a rule, a decrease or an increase of isotopomers is observed here (transients) (FIG. 6).

Real fluxes can be calculated with the aid of a stoichiometric plant metabolism model by comparing theoretically calculated and experimentally recorded transients.

Example 7: Flux Analyses on Intact Rice Plants

Intact rice plants (seedlings) were $^{13}CO_2$-labeled in a labeling chamber according to the invention for. To this end, 16 rice seedlings as a whole in their plant containers were acclimatized in a greenhouse chamber under normal atmosphere over a period of 10 days. At the beginning of the experiment, the plants were placed into the labeling chamber. Thereafter, the atmosphere in the chamber was purged from ambient $^{12}CO_2$ by being passed through the gas absorption unit over a 45-sec period at an air-flow rate of 2500 l/min. The $CO_2$ content of the purged air was thereby reduced to approximately 20 ppm. Thereafter, the $^{13}CO_2$ content of the chamber atmosphere was brought to 400 ppm by immediately injecting 300 ml of $^{13}CO_2$ into the chamber through the injection duct.

To obtain the aerial green biomass of the individual rice seedlings as completely as possible as the sample, the rice seedlings as a whole (without roots) were cut off as closely as possible above the soil surface of the plant container using cut-and-hold shears, removed through the lock and immediately frozen in liquid nitrogen. By using the chamber according to the invention, it was possible to carry out this process within 1 to 2 seconds.

The first sample was taken simultaneously with the $^{13}CO_2$ feeding. Further samples were taken in each case 10, 20, 30, 40, 50, 60, 90, 120, 150, 180, 240, 300, 420, 600 and 900 seconds after feeding of the $^{13}CO_2$.

The resulting 16 samples were processed as described in Example 5. The experiment was repeated in total three times, so that three samples were available for each of the 16 points in time for measuring the $^{13}CO_2$ incorporation into the various metabolites. As described in Example 6, it was possible to calculate transients for the following metabolites from the averaged measured values of the respective different isotopomers: 3-phosphoglycerate (see FIG. 6), citrate, malate, ribose-5-phosphate, ribulose-5-phosphate, fructose-6-phosphate, fructose-1,6-bisphosphate, isocitrate, sedoheptulose-7-phosphate, glucose-6-phosphate, succinate, dihydroxyacetone phosphate, phosphoenolpyruvate.

The exemplary transient plots of the different mass isotopomers of 3-phosphoglycerate (FIG. 6: M0, M1, M2, M3) demonstrate the necessity of rapid and frequent sampling within the first 120 seconds after converting the atmosphere to $^{13}CO_2$, which was only made possible by the labeling chamber according to the invention and in particular the lock used for sampling:

Only the use of the chamber according to the invention, equipped with the lock, makes possible a resolution, of the transient courses, over time—in particular of metabolites with rapid $^{13}CO_2$ incorporation (high conversion rate) and thus of the incorporation of the labeled carbon dioxide.

By bringing the data obtained into line with an isotopic-dynamic model of the metabolism of the plant, it was possible for the first time to establish what is known as a flux map for an intact crop plant (a rice seedling).

We claim:

1. An isotope labeling chamber for labeling metabolites in an organism, comprising a reactor chamber (1) and an air regulation chamber (2), wherein
    the reactor chamber (1) comprises: an optional housing frame (3), housing walls (4), at least one injection valve (5), wherein at least one housing wall (4) can be opened fully and/or in part and wherein at least one housing wall comprises a lock (6) adapted to permit sampling through the lock, of an organism growing in the reactor chamber without gas exchange between the reactor chamber and the external environment to the reactor chamber, and
    the air regulation chamber (2) further comprises: a temperature-regulating unit (7), an air humidification unit (8), and a carbon dioxide gas absorption unit (9) comprising a material which absorbs carbon dioxide.

2. The isotope labeling chamber according to claim 1, wherein the air regulation chamber (2) further comprises a pressure-relief valve (10) and a vacuum valve (11).

3. The isotope labeling chamber according to claim 1, wherein the at least one housing wall which can be opened fully and/or in part is a door.

4. The isotope labeling chamber according to claim 1, wherein the lock (6) is a component of the door or of one of the walls.

5. The isotope labeling chamber according to claim 1, wherein the housing walls are composed of polycarbonate.

6. The isotope labeling chamber according to claim 5, wherein the housing walls have a thickness of from 3 to 11 mm.

7. The isotope labeling chamber according to claim 1, wherein the housing frame is present and comprises aluminum.

8. The isotope labeling chamber according to claim 1, wherein the housing frame is present and is further provided with a sealant.

9. The isotope labeling chamber according to claim 1, wherein the temperature-regulating unit (7) is provided with at least one blower (25).

10. The isotope labeling chamber according to claim 1, wherein the air humidification unit (8) comprises a piezo-ceramic ultrasonic transducer (32).

11. The isotope labeling chamber according to claim 1, wherein the material which absorbs carbon dioxide is soda lime.

12. The isotope labeling chamber according to claim 1, wherein the lock (6) comprises at least two expandable bands (20) which overlap in the shape of a cross or a star.

13. A method for labeling plants with stable isotopes, the method comprising:
    positioning a plant within the isotope labeling chamber according to claim 1; and
    isotopically labeling the plant inside the chamber.

14. The method according to claim 13, wherein the plants are maize, rice, wheat, soybeans, or oilseed rape.

15. The isotope labeling chamber according to claim 6, wherein the housing walls have a thickness of from 5 to 9 mm.

* * * * *